(12) United States Patent
Liang et al.

(10) Patent No.: US 10,654,038 B2
(45) Date of Patent: May 19, 2020

(54) NUCLEIC ACID ANALYSIS APPARATUS

(71) Applicant: Delta Electronics Int'l (Singapore) Pte Ltd, Singapore (SG)

(72) Inventors: Qian Liang, Singapore (SG); Bo Ma, Singapore (SG); Shuwen An, Singapore (SG); Weishi Zhang, Singapore (SG)

(73) Assignee: DELTA ELECTRONICS INT'L (SINGAPORE) PTE LTD, Singapore (SG)

( * ) Notice: Subject to any disclaimer, the term of this patent is extended or adjusted under 35 U.S.C. 154(b) by 109 days.

(21) Appl. No.: 15/700,791

(22) Filed: Sep. 11, 2017

(65) Prior Publication Data

US 2018/0071728 A1 Mar. 15, 2018

Related U.S. Application Data (60) Provisional application No. 62/393,211, filed on Sep. 12, 2016, provisional application No. 62/393,223, filed on Sep. 12, 2016.

(51) Int. Cl.
*B01L 3/00* (2006.01)
*B01L 7/00* (2006.01)
*C12N 15/10* (2006.01)

(52) U.S. Cl.
CPC ......... *B01L 3/502* (2013.01); *B01L 3/502715* (2013.01); *B01L 7/00* (2013.01);
(Continued)

(58) Field of Classification Search
CPC ...... B01L 3/502; B01L 7/00; B01L 3/502715; B01L 7/52; B01L 2300/0803; B01L 2300/0832; B01L 2300/0627; B01L 2200/16; B01L 2200/10; B01L 2200/0631; B01L 2200/025; B01L 2200/143; B01L 3/527; B01L 2400/0409; C12N 15/1003
See application file for complete search history.

(56) References Cited

U.S. PATENT DOCUMENTS 6,783,736 B1 8/2004 Taylor
8,441,629 B2 5/2013 Kolesnychenko et al.
(Continued)

FOREIGN PATENT DOCUMENTS

CN 101156059 B 6/2011
CN 103831140 A 6/2014
(Continued)

*Primary Examiner* — Gautam Prakash
(74) *Attorney, Agent, or Firm* — Kirton McConkie; Evan R. Witt (57) ABSTRACT

A nucleic acid analysis apparatus with isothermal based amplification includes a chamber, a fluid delivery unit, a thermal unit, a rotational driven unit and at least one optical unit. The chamber includes a cartridge mounted therein. The fluid delivery unit is connected with the chamber and adapted to transport reagents within the cartridge for sample purification and/or nucleic acid extraction. The thermal unit is disposed in the chamber and adapted to provide a predefined temperature for nucleic acid amplification. The rotational driven unit is connected with the chamber and capable of rotating the cartridge with a predefined program. The at least one optical unit is disposed on the chamber and includes plural optical components for detection.

18 Claims, 8 Drawing Sheets

(52) U.S. Cl.
CPC ............ *B01L 7/52* (2013.01); *C12N 15/1003*
(2013.01); *B01L 3/527* (2013.01); *B01L 2200/025* (2013.01); *B01L 2200/0631* (2013.01); *B01L 2200/10* (2013.01); *B01L 2200/143* (2013.01); *B01L 2200/16* (2013.01); *B01L 2300/0627* (2013.01); *B01L 2300/0803* (2013.01); *B01L 2300/0832* (2013.01); *B01L 2400/0409* (2013.01)

(56) References Cited

U.S. PATENT DOCUMENTS

| | | |
|---|---|---|
| 2005/0233324 A1 | 10/2005 | Corbett et al. |
| 2006/0040303 A1 | 2/2006 | Weilke |
| 2006/0204997 A1* | 9/2006 | Macioszek et al. .. C12Q 1/6851 435/6.11 |
| 2006/0223061 A1 | 10/2006 | Corbett et al. |
| 2008/0153078 A1* | 6/2008 | Brannan et al. ........ B01L 3/502 435/2 |
| 2009/0221059 A1* | 9/2009 | Williams et al. ..... B01L 3/5027 435/287.2 |
| 2010/0086990 A1 | 4/2010 | Stanley et al. |
| 2011/0044865 A1* | 2/2011 | Groisnnan et al. ..... B01L 9/527 422/503 |
| 2014/0004621 A1* | 1/2014 | Dority et al. .......... B01L 3/502 436/178 |

FOREIGN PATENT DOCUMENTS

| | | |
|---|---|---|
| CN | 105828945 A | 8/2016 |
| CN | 105940094 B | 2/2018 |
| JP | 2012-524242 A | 10/2012 |
| TW | M445583 | 1/2013 |
| TW | 201617454 A | 5/2016 |
| TW | 201704477 A | 2/2017 |
| WO | WO 98/49340 * | 5/1998 |
| WO | 2004046719 A1 | 6/2004 |

* cited by examiner

NUCLEIC ACID ANALYSIS APPARATUS

CROSS-REFERENCE TO RELATED APPLICATION

This application claims the benefit of U.S. Provisional Application Ser. No. 62/393,211 filed on Sep. 12, 2016, and claims the benefit of U.S. Provisional Application Ser. No. 62/393,223 filed on Sep. 12, 2016, the entire contents of which are incorporated herein by reference for all purposes.

FIELD OF THE INVENTION

The present invention relates to a nucleic acid analysis apparatus, and more particularly to a nucleic acid analysis apparatus with isothermal based amplification.

BACKGROUND OF THE INVENTION

Point-of-care (POC) testing is an analytical method conducted outside the central hospital and/or laboratory using devices that can instantly interpret the results. With the increasing threat of accelerated epidemic-to-pandemic transitions of new or reemerging infectious disease outbreaks owing to globalization, decentralizing diagnostic testing at frontline clinical settings could facilitate earlier implementations of public health responses to contain and mitigate such events. In the developing countries where high infectious disease burden is compounded by diagnostic challenges due to poor clinical laboratory infrastructure and cost constraints, the potential utility for POC testing is even greater.

Although microbial culture, microscopy examination and metabolites biochemical test are still used in some scenarios, today the majority of POC device and assay development are different types of PCR (polymerase chain reaction, such as nested PCR, real-time PCR and digital PCR) based methods. PCR is an enzyme-driven process for amplifying short regions of DNA in vitro where millions of DNA copies are created by cycling among different temperatures to allow repeating steps (denaturation, annealing and elongation) of DNA replication to take place. Despite the simplicity and amplification power of PCR chemistry, requirement of precision thermal cycling among two or three temperature zones during the reaction is an inevitable drawback for PCR development in POC diagnostics.

Above mentioned limitations of the PCR reaction stimulates the development of alternative isothermal amplification methods. Instead of using thermal cycling, isothermal amplification relies on proteins that use in vivo mechanisms of DNA/RNA synthesis and dominated by enzyme activity. Therefore, miniaturize isothermal system has advantages of simple design and extremely low energy consumption. Today, various isothermal based amplification methods in terms of assay complexity (multiple enzymes or primers), acceptable detection sensitivity, and specificity have been developed, including nucleic acid sequence-based amplification (NASBA), strand displacement amplification (SDA), helicase-dependent amplification (HDA), loop-mediated isothermal amplification (LAMP), recombinase polymerase amplification (RPA) and nicking enzyme amplification reaction (NEAR).

As a relative new solution, the platform design of isothermal method lags behind its biochemical technique development. Because isothermal amplification bears higher tolerance on the sample purity, most of commercial isothermal platforms focus on creating a stable temperature environment and detection methods with middle and high throughput. The sample preparation, however, is carried out either using external equipment or manual operation. On the other hand, with the increasingly demand of simultaneously detection of multi targets, the ability of multiplexing is inevitable for isothermal based POC platforms. Unfortunately, there is no all-in-one commercial platform being able to detect multiple targets with isothermal amplification methods.

Thus, there is a need of providing an all-in-one nucleic acid analysis apparatus with isothermal based amplification to overcome the drawbacks of the prior arts.

SUMMARY OF THE INVENTION

An object of the embodiment of the present invention is to provide an all-in-one nucleic acid analysis apparatus with isothermal based amplification, so that the processes of sample purification, nucleic acid extraction, nucleic acid amplification and/or nucleic acid detection may be performed on the all-in-one apparatus to realize nucleic acid analysis in real time.

Another object of the embodiment of the present invention is to provide a nucleic acid analysis apparatus capable of simultaneously detecting multiple targets with isothermal based amplification.

According to an aspect of the embodiment of the present invention, there is provided a nucleic acid analysis apparatus with isothermal based amplification, including a chamber, a fluid delivery unit, a thermal unit, a rotational driven unit, and at least one optical unit. The chamber includes a cartridge mounted therein. The fluid delivery unit is connected with the chamber and adapted to transport reagents within the cartridge for sample purification and/or nucleic acid extraction. The thermal unit is disposed in the chamber and adapted to provide a predefined temperature for nucleic acid amplification. The rotational driven unit is connected with the chamber and capable of rotating the cartridge with a predefined program. The at least one optical unit is disposed on the chamber and includes plural optical components for detection.

In an embodiment of the present invention, the chamber is able to be opened and includes a top chamber and a bottom chamber.

In an embodiment of the present invention, the cartridge is mounted in a cavity of the bottom chamber.

In an embodiment of the present invention, the nucleic acid analysis apparatus further includes at least one fixing component, and during sample purification and/or nucleic acid extraction, the cartridge is locked on the chamber by the at least one fixing component to contact the fluid delivery unit tightly.

In an embodiment of the present invention, the fixing component includes a clip, and the cartridge includes a lock slot capable of being engaged with the clip.

In an embodiment of the present invention, the chamber further includes a release actuator to unlock the cartridge.

In an embodiment of the present invention, the cartridge includes a detection chip and a reagent storing body, and the detection chip is disposed on the top of the reagent storing body.

In an embodiment of the present invention, the detection chip is a planar fluidic chip and includes plural detection wells and at least one microchannel connected with the detection wells.

In an embodiment of the present invention, each of the detection wells has at least one planar surface.

In an embodiment of the present invention, the shape of the detection chip is substantially a regular polygon.

In an embodiment of the present invention, the chamber further includes at least one positioning component, and the detection chip includes at least one alignment slot capable of being aligned with the at least one positioning component on the chamber.

In an embodiment of the present invention, the reagent storing body includes plural reagent cells used to store reagents for sample purification and nucleic acid extraction.

In an embodiment of the present invention, the detection chip further includes at least one opening at a top surface of the detection chip for adding sample.

In an embodiment of the present invention, the thermal unit includes a heater, a heat spreader, and plural fan blades.

In an embodiment of the present invention, the fan blades are mounted on and driven by the rotational driven unit, and a rotation of the fan blades generates air flow towards the heat spreader to accelerate the thermal mixing within the chamber.

In an embodiment of the present invention, the rotational driven unit includes a step motor to rotate the cartridge at a predefined angle.

In an embodiment of the present invention, the rotational driven unit includes a cartridge clamp used to clamp and rotate the cartridge during nucleic acid amplification and/or detection.

In an embodiment of the present invention, the cartridge clamp includes a magnetic component, and the cartridge includes an embedded magnetic material, so that a magnetic force between the magnetic component and the magnetic material attracts the cartridge to move toward the cartridge clamp.

In an embodiment of the present invention, the optical unit includes a light source and an optical detector.

In an embodiment of the present invention, the nucleic acid analysis apparatus includes multiple optical units, and each optical unit offers a unique color of illumination to detect multiple targets.

The above objects and advantages of the embodiments of the present invention become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of the embodiments of this invention are presented herein for purpose of illustration and description only; it is not intended to be exhaustive or to be limited to the precise form disclosed.

The embodiment of the present invention provides a nucleic acid analysis apparatus with isothermal based amplification. More particularly, the embodiment of the present invention provides an all-in-one nucleic acid analysis apparatus with isothermal based amplification, which integrates a fluid delivery unit, a thermal unit, a rotational driven unit, and an optical unit on one single device, so that the processes of sample purification, nucleic acid extraction, nucleic acid amplification and nucleic acid detection can be performed on the all-in-one apparatus to realize nucleic acid analysis in real time.

Figure 1:
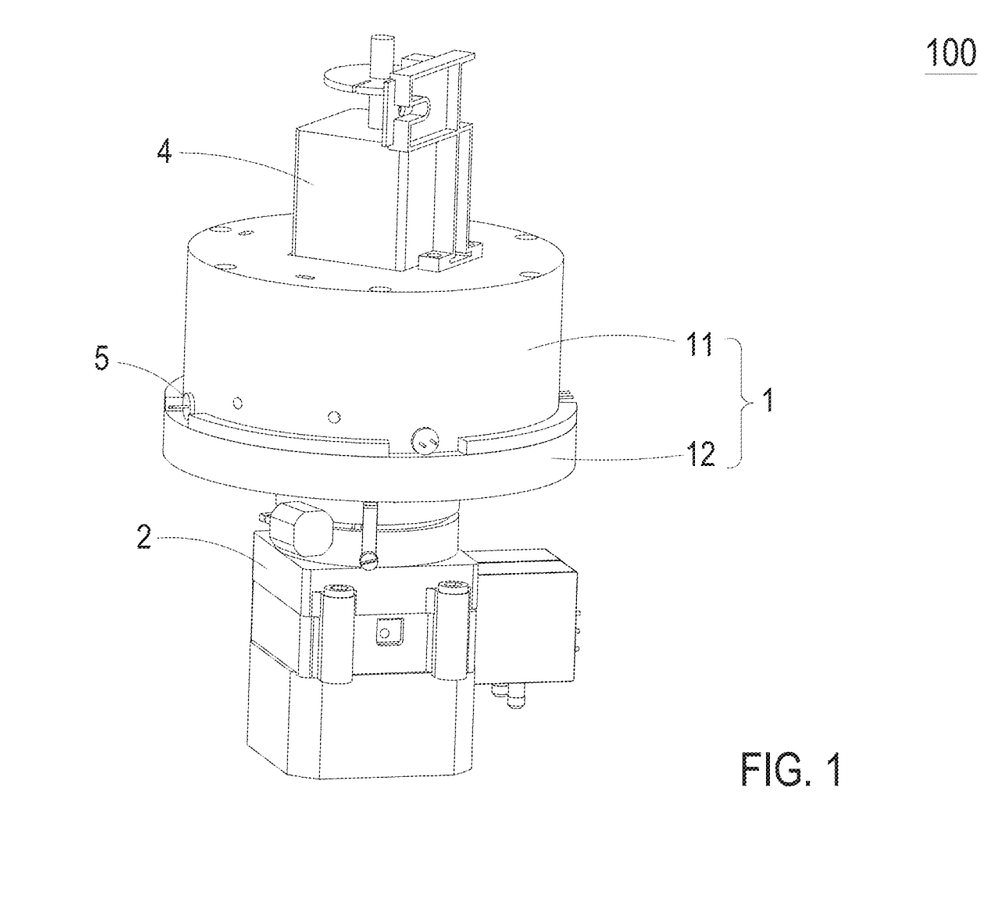
FIG. 1 shows a schematic view of the nucleic acid analysis apparatus according to the embodiment of the present invention.
Figure 2:
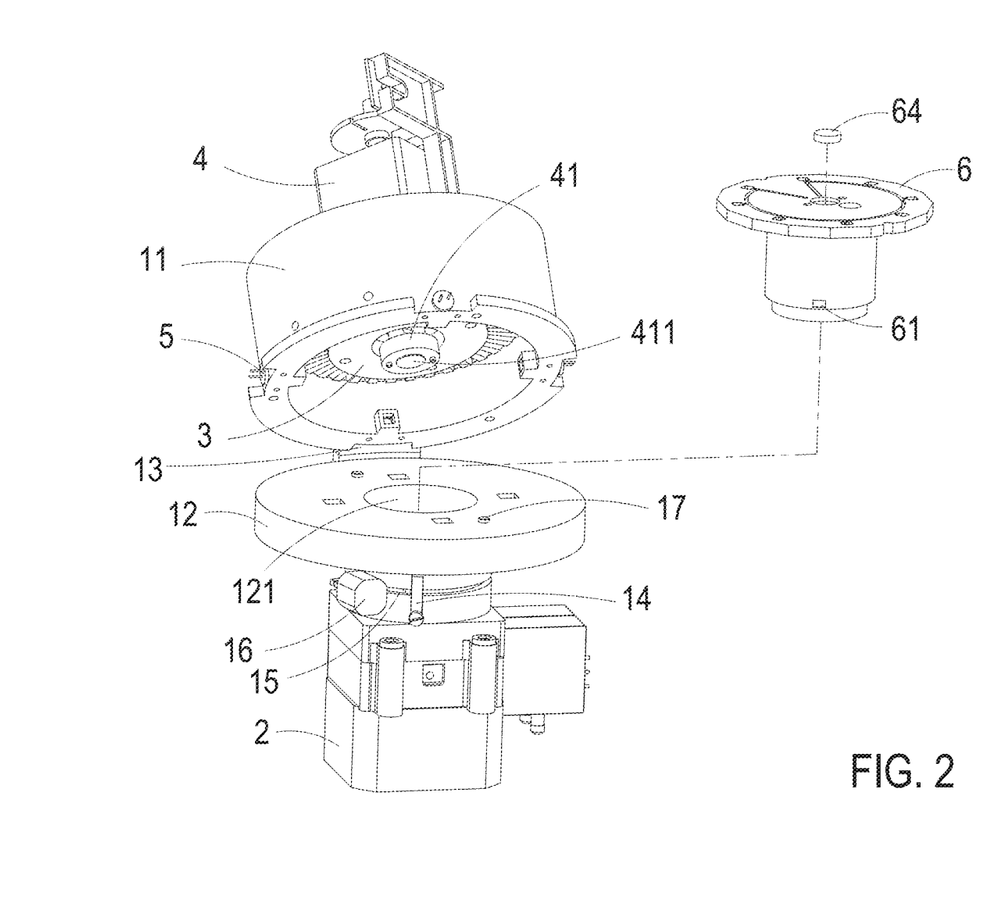
FIG. 2 shows the nucleic acid analysis apparatus of FIG. 1 with opened chamber.

FIG. 1 shows a schematic view of the nucleic acid analysis apparatus according to the embodiment of the present invention, and FIG. 2 shows the nucleic acid analysis apparatus of FIG. 1, wherein the nucleic acid analysis apparatus is opened, and the cartridge is moved out of the nucleic acid analysis apparatus. As shown in FIGS. 1 and 2, the nucleic acid analysis apparatus 100 includes a chamber 1, a fluid delivery unit 2, a thermal unit 3, a rotational driven unit 4, and at least one optical unit 5. The chamber 1 is able to be opened for mounting a cartridge 6 therein. The fluid delivery unit 2 is connected with the chamber 1 and adapted to transport reagents within the cartridge 6 for sample purification and/or nucleic acid extraction. The thermal unit 3 is disposed in the chamber 1 and adapted to provide a predefined temperature for nucleic acid amplification. The rotational driven unit 4 is connected with the chamber 1 and capable of rotating the cartridge 6 within the chamber 1 with a predefined program. In an embodiment, the rotational driven unit 4 is able to clamp the cartridge 6. The least one optical unit 5 is disposed on the chamber 1 and includes plural optical components for detection, such as nucleic acid detection or sample reaction detection.

In an embodiment, the chamber 1 includes a top chamber 11 and a bottom chamber 12. The top chamber 11 and the bottom chamber 12 are connected through a hinge 13, but not limited thereto. The bottom chamber 12 has a cavity 121 specifically designed for mounting the cartridge 6 therein. The top chamber 11 can be opened, so that the cartridge 6 is able to be placed into the cavity 121 of the bottom chamber 12. When the top chamber 11 is closed, a confined space is formed in the chamber 1.

In an embodiment, the shape of the chamber 1 could be but not limited as cylindrical, spherical, cubic, conical or olivary, and the chamber 1 could be made but not limited by metal, ceramic, polymer, polymer compound, wood, glass, or other materials as long as it is able to provide good thermal insulation.

The bottom chamber 12 is connected with the fluid delivery unit 2 through tubing or channels. Once the cartridge 6 is mounted in bottom chamber 12, the cartridge 6 is locked and forced to tightly contact the fluid delivery unit 2 without leakage. For example, the cartridge 6 is locked on the bottom chamber 12 by at least one fixing component, such as a clip but not limited thereto.

Figure 3:
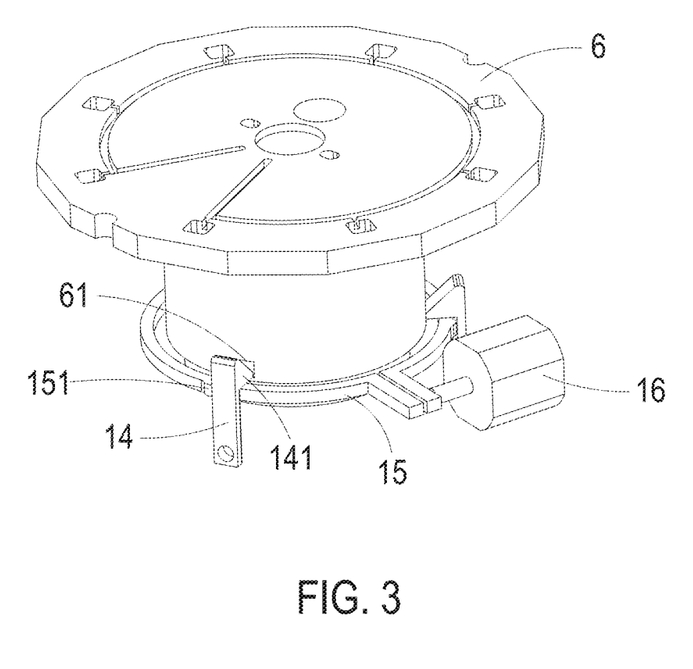
FIG. 3 shows the lock and release mechanism between the cartridge and the bottom chamber.

FIG. 3 shows the lock and release mechanism between the cartridge and the bottom chamber. As shown in the embodiment of FIGS. 2 and 3, the cartridge 6 includes at least one lock slot 61 on its cylindrical body, and the bottom chamber 12 includes at least one clip 14, a release ring 15, and a release actuator 16. The clip 14 is fixed at the bottom and has a hook 141 on the top. The clip 14 could be made by polymer or metal strip with elasticity. When the cartridge 6 is placed into the cavity 121 of the bottom chamber 12, the user pushes the cartridge 6 downwardly to make the hook 141 of clip 14 be engaged and locked with the lock slot 61 of the cartridge 6, and thus make the cartridge 6 tightly contact the fluid delivery unit 2. The release ring 15 surrounds the cylindrical body of the cartridge 6, and leans against the bottom surface of the hook 141. The release ring 15 is able to slide within a certain distance, and is connected with the release actuator 16, such as a solenoid actuator. When the cartridge 6 is to be released, the release actuator 16 is triggered to drag the release ring 15, then the convex structure 151 on the release ring 15 pushes the clip 14 to separate the hook 141 apart from the lock slot 61 and therefore release the cartridge 6.

In an embodiment, the clip 14 could be operated by user manually or by the device automated on demand. Certainly, the lock and release mechanism is not limited to the clip 14 described above, and may be other fixing component as long as it is able to lock and release the cartridge 6.

Figure 4:
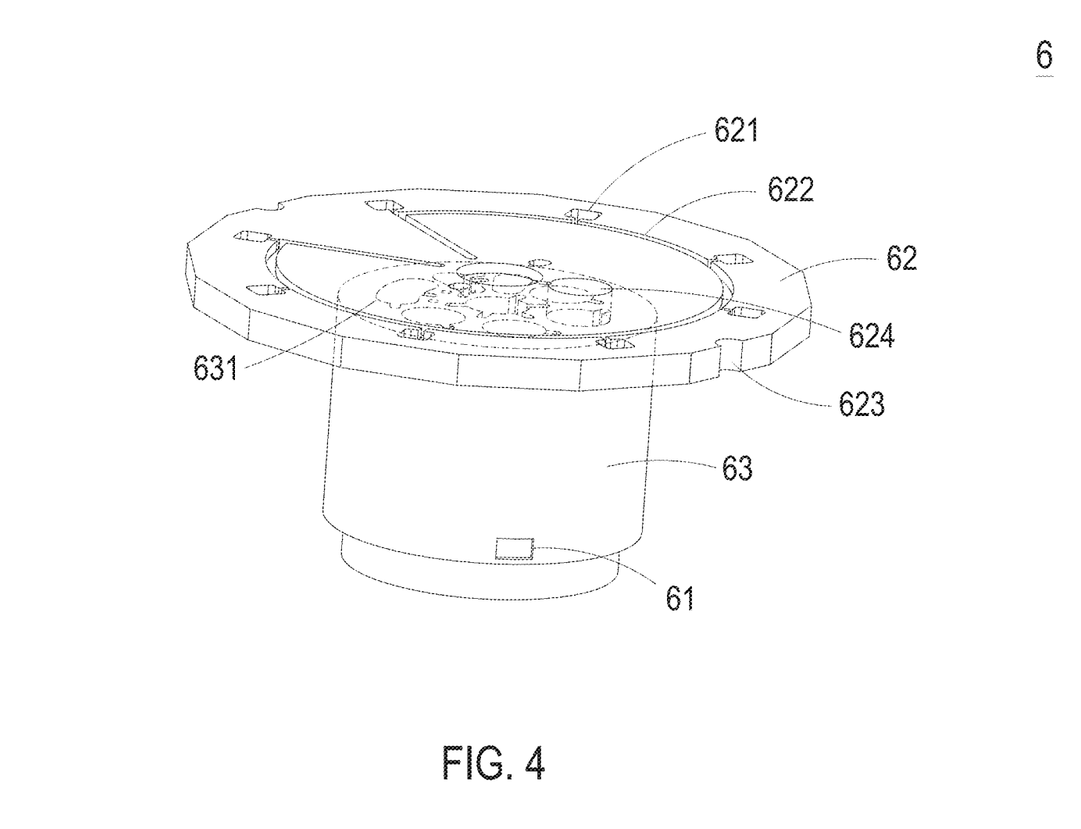
FIGS. 4 and 5 show different views of the cartridge.
Figure 5:
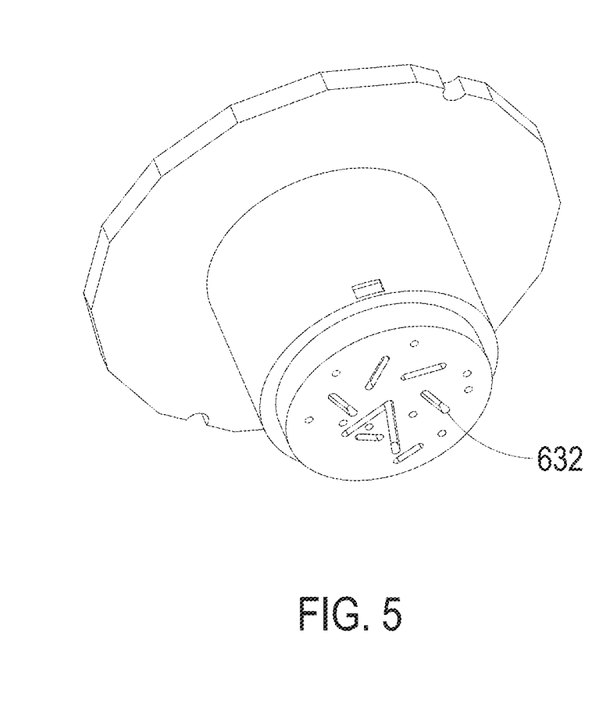

FIGS. 4 and 5 show different views of the cartridge. As shown in FIGS. 4 and 5, the cartridge 6 includes a detection chip 62 and a reagent storing body 63, and the detection chip 62 is disposed on the top of the reagent storing body 63. The detection chip 62 is a planar fluidic chip, and includes plural detection wells 621 and at least one microchannel 622 connected with the detection wells 621. In an embodiment, the detection wells 621 include reagents for nucleic acid amplification and/or detection. For example, the detection wells 621 may be coated with reagents for nucleic acid amplification and/or detection, such as reagents containing different fluorescent dyes.

The number of the detection wells 621 is not limited, and may be 40 or even more, and the apparatus could perform multiplexing nucleic analysis. In an embodiment, the shape of the detection chip 62 is substantially a regular polygon, so that the detection chip 62 has plural planar side surfaces to be in line with the optical unit 5 to facilitate light focusing. Certainly, the shape of the detection chip 62 is not limited to the regular polygon and it may also be circular or other shape, since the light could be focused on the sample in the detection well 621 by the arrangement of optical components of the optical unit 5.

In an embodiment, the detection chip 62 further includes at least one alignment slot 623, and the bottom chamber 12 further include at least one positioning component 17 (as shown in FIG. 2). For example, the positioning component 17 includes a positioning pin. When the cartridge 6 is placed into the cavity 121 of the bottom chamber 12, the alignment slot 623 of the cartridge 6 is aligned with the positioning component 17 of the bottom chamber 12, which helps an easy cartridge loading, and accordingly, the cartridge 6 may be self-aligned with the fluid delivery unit 2 through channels or tubing on the bottom chamber 12, and each optical unit 5 is in line with one of the detection wells 621. In an embodiment, each of the detection wells 621 has at least one planar surface. For example, the detection well 621 may be rectangular-shaped and have one planar surface in line with a light source of the optical unit 5 and another planar surface in line with an optical detector of the optical unit 5, respectively, during nucleic acid detection.

The reagent storing body 63 includes plural reagent cells 631 used to store reagents for sample purification and/or nucleic acid extraction. The reagent storing body 63 also includes plural channels connected with the reagent cells 631 for fluid delivery. In an embodiment, the reagent storing body 63 is but not limited to a cylindrical body. The reagent storing body 63 further includes plural openings 632 at the bottom surface of the reagent storing body 63, and the openings 632 are communicated with the reagent cells 631 through the channels. The shape of the openings 632 may be but not limited to circular, linear or other regular or irregular shape.

The detection chip 62 further includes at least one opening 624 at the top surface of the detection chip 62, and the opening 624 aligns and communicates with at least on reagent cell 631 of the reagent storing body 63 for adding sample to the cartridge 6.

The fluid delivery unit 2 works concurrently with the cartridge 6 to carry out sample purification, nucleic acid extraction and fluid delivery so as to have a fully automatic device. The fluid delivery unit 2 is similar to the integrated fluidic module of U.S. patent application Ser. No. 15/217,511 filed on Jul. 22, 2016, which claims the priority to Singapore Patent Application No. 10201605723Y filed on Jul. 13, 2016, by the applicant of the present invention, the entire contents of which are incorporated herein by reference and are not redundantly described here. In brief, the fluid delivery unit 2 of the present invention includes the fluid manifold, the valve stator, the valve rotor, the valve housing and the fluid sources as disclosed in U.S. patent application Ser. No. 15/217,511. The fluid manifold includes plural microchannels for connecting with the reagent cells 631 of the cartridge 6 through the bottom openings 632. By the alignments of the through holes and/or grooves of the valve stator and the valve rotor, multi-way fluid path switching is realized when the valve rotor is rotated to different positions, so as to regulate the fluid operations in the cartridge 6. Thereby, the reagents stored within the cartridge 6 are able to be transported to desired locations through pneumatic force from pumps of the fluid delivery unit 2, so as to automatically perform the sample purification and the nucleic acid extraction. Certainly, the fluid delivery unit 2 is not limited to the above-mentioned design, and can be any other type as long as it is able to realize multiple fluid delivery and multi-way fluid path switching in the cartridge 6.

Figure 6:
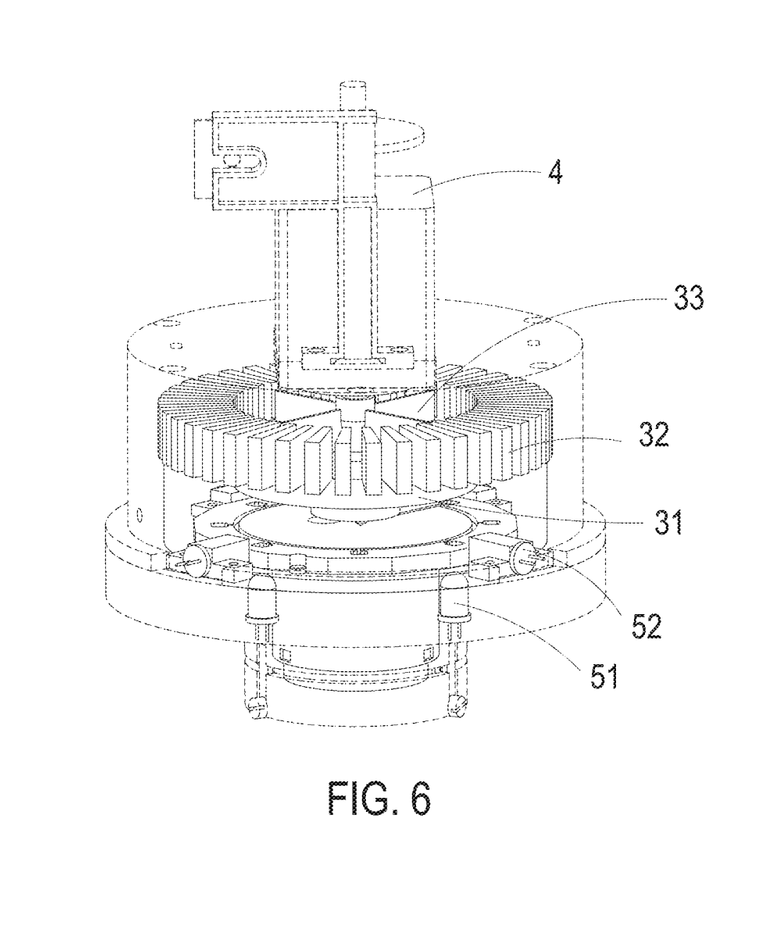
FIG. 6 shows the internal structures in the chamber of the nucleic acid analysis apparatus.

FIG. 6 shows the internal structures in the chamber of the nucleic acid analysis apparatus, wherein the fluid delivery unit 2 is removed and the outlines of the chamber 1 and the rotational driven unit 4 are shown by broken lines to more clearly show the internal structures in the chamber. As shown in FIGS. 2 and 6, the thermal unit 3 includes a heater 31, a heat spreader 32, and plural fan blades 33. The heat spreader 32 includes plural heat sinks surrounding the heater 31 and is mounted on the heater 31 so that the generated heat could be spread rapidly. The fan blades 33 are mounted on and driven by the rotational driven unit 4, and the rotation of the fan blades 33 generates air flow towards the heat spreader 32 to accelerate the thermal mixing within the closed chamber 1.

The nucleic acid analysis apparatus 100 is designed to amplify nucleic acid based on isothermal method and therefore only a constant temperature instead of thermal cycling among three different temperature zones is needed. As a result, the thermal unit 3 is significantly simplified. In addition, the chamber 1 of the nucleic acid analysis apparatus 100 is designed with superior thermal insulation and therefore the inner temperature is easily been maintained. Once the chamber 1 is in a uniform temperature environment, heat loss from the detection wells 621 and sample towards the environment could be minimized. At the amplification and/or detection processes, the whole closed chamber 1 and the sample at each detection well 621 are substantially in the same temperature, regardless the cartridge 6 is in motion or in stationary.

The thermal unit 3 provides the required temperature within the chamber 1 during the operation, wherein the temperature control is independent of the number and shape of detection wells 621. In an embodiment, the thermal unit 3 further includes a temperature sensor to control the accuracy of the temperature.

In an embodiment, the thermal unit 3 heats up the sample though non-contact approaches, such as hot air convection, heat dissipating, infrared heating, microwave heating and laser heating, but not limited thereto.

In an embodiment, the thermal unit 3 includes detachable heaters which may contact the detection well 621 during the amplification for good heat transfer purpose, and the heaters are able to be detached from the cartridge 6, allowing the cartridge 6 in motion when necessary.

The rotational driven unit 4 is mounted on the top chamber 11. The rotational driven unit 4 is but not limited to a motor, and it may also be solenoid, manual operation, spring, clockwork or other components, and is able to clamp and rotate the cartridge 6 at predefined angles and pass each detection well 621 in alignment with each optical unit 5 sequentially. In an embodiment, the rotational driven unit 4 includes a step motor, which is able to drive both rotations of the fan blades 33 and the cartridge 6 in different patterns.

Figure 7:
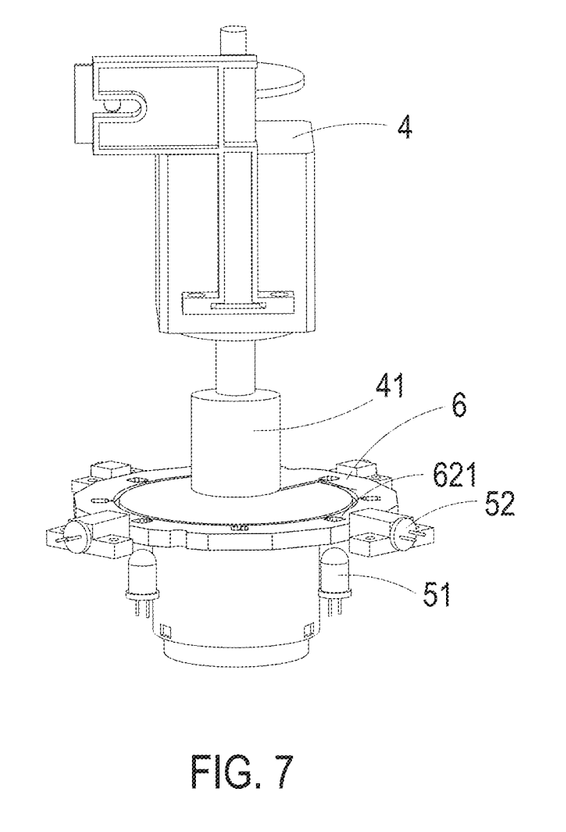
FIG. 7 shows the structures of the rotational driven unit, the cartridge, and the optical unit.

FIG. 7 shows the structures of the rotational driven unit 4, the cartridge 6 and the optical unit 5. As shown in FIGS. 2 and 7, the rotational driven unit 4 further includes a cartridge clamp 41 used to clamp and rotate the cartridge 6. Once the cartridge 6 is clamped, it is able to rotate within the chamber 1, actuated by the rotational driven unit 4. Various mechanisms are capable of realizing cartridge clamp and release on demand. In an embodiment, the cartridge clamp 41 includes a magnetic component 411, and for example, the magnetic component 411 includes a magnet. Accordingly, a magnetic material 64 is embedded within the detection chip 62 of the cartridge 6 during the manufacture of the cartridge 6, and for example, the magnetic material 64 includes iron. When the cartridge 6 is locked by the clip 14, a tiny gap around 0.5 mm to 3 mm exists between the top surface of the cartridge 6 and the cartridge clamp 41. In this situation, the rotational driven unit 4 actuates the fan blades 33 only. Once the cartridge 6 is released from the clip 14, the magnetic force between the magnetic component 411 and the magnetic material 64 attracts the cartridge 6 to move toward the cartridge clamp 41, so that the cartridge 6 is held and fixed by the cartridge clamp 41 of the rotational driven unit 4. Thus, the cartridge 6 could freely rotate within the chamber 1 during the nucleic acid amplification and/or detection, and there is a tiny gap between the bottom surface of the cartridge 6 and the fluid delivery unit 2.

In other embodiments, the cartridge clamp 41 may also be solenoid, screw, nut, press fitted parts, frictional parts, grip, pincer, epoxy, chemical bonding or other types as long as it is able to clamp the cartridge 6 on demand.

In an embodiment, the nucleic acid analysis apparatus 100 includes multiple optical units 5. The optical unit 5 has optical components such as light source, lens, filter and optical detector to realize the optical detection so that the sample could be detected in real time during the nucleic acid amplification. As shown in FIGS. 6 and 7, the optical unit 5 includes at least one light source 51 and at least one optical detector 52. The light source 51, such as LED, is embedded within the chamber 1. During the operation, each light source 51 aligns to one of the detection wells 621 of the cartridge 6 in order to offer effective illumination for detection. Once the cartridge 6 is clamped, the optical detector 52, such as photodiode, is in line with one of the detection wells 621 on the cartridge 6 and therefore the results of nucleic acid analysis are interpreted. The rotation of the cartridge 6 allows each detection well 621 pass through different optical units 5 sequentially. In an embodiment, each optical unit 5 could offer a unique color of illumination so as to provide different colors for fluorescent based detection, and thus, the nucleic acid analysis apparatus 100 can detect multiple targets simultaneously and realize multiplexing detection.

In an embodiment, the nucleic acid analysis apparatus 100 includes a controller, which controls the operations of the fluid delivery unit 2, the thermal unit 3, the rotational driven unit 4 and the optical unit 5. In an embodiment, the controller may also control the release of the clip 14.

By utilizing the isothermal based amplification, the thermal unit 3 is significantly simplified, and thus, the nucleic acid analysis apparatus 100 can be compact designed and is even smaller than a common teacup. In an embodiment, the nucleic acid analysis apparatus 100 has a height ranged between 100 mm and 120 mm and a width ranged between 80 mm and 100 mm. Since the nucleic acid analysis apparatus 100 is cup sized, it is portable and suitable for POC diagnostics.

The nucleic acid analysis apparatus 100 is designed for isothermal based amplification, and thus can be used to perform all isothermal amplification methods, such as nucleic acid sequence-based amplification (NASBA), strand displacement amplification (SDA), helicase-dependent amplification (HDA), loop-mediated isothermal amplification (LAMP), recombinase polymerase amplification (RPA) and nicking enzyme amplification reaction (NEAR).

Figure 8:
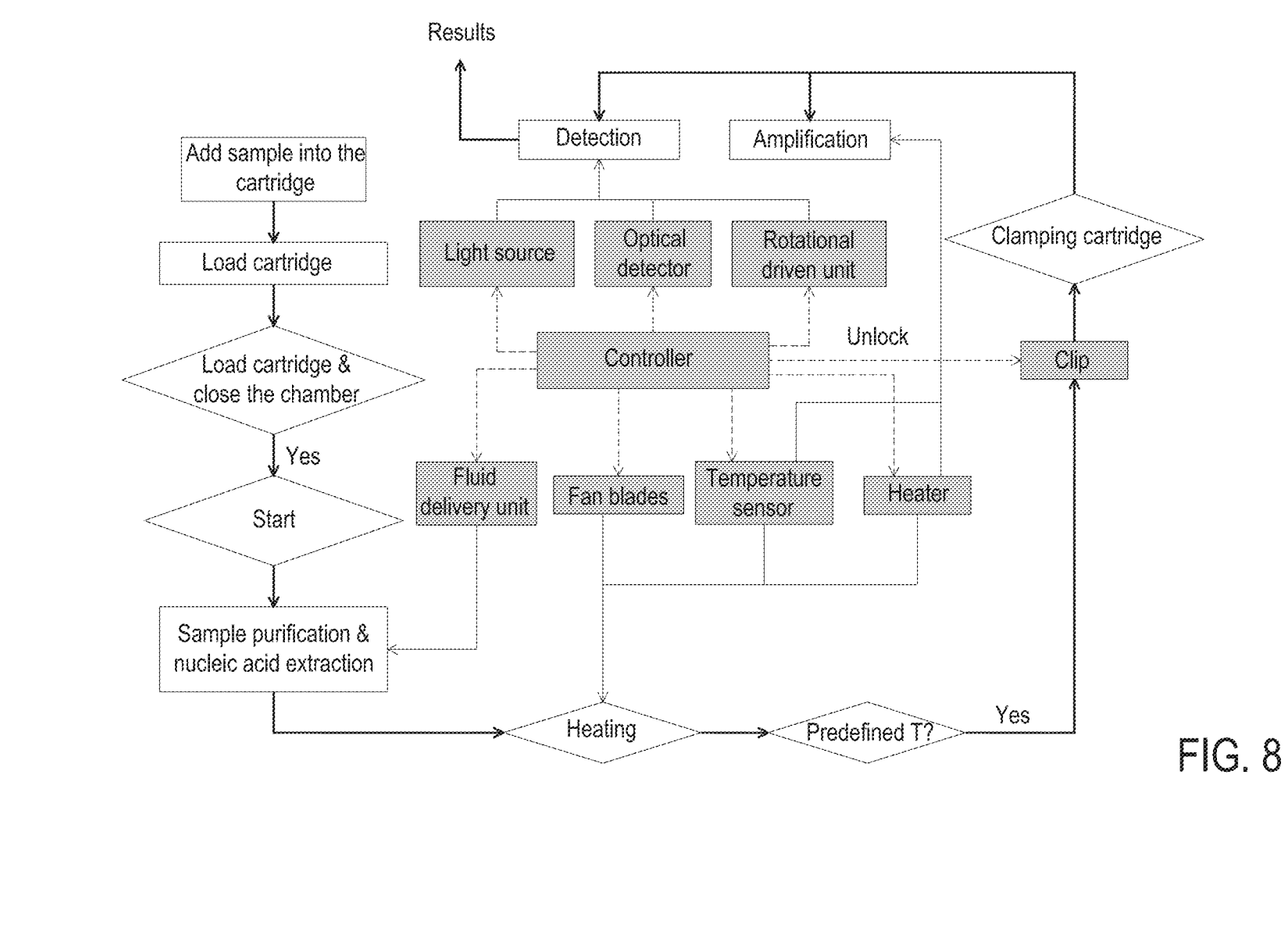
FIG. 8 shows the flow chart of the operation of the nucleic acid analysis apparatus.

FIG. 8 shows the flow chart of the operation of the nucleic acid analysis apparatus. The thick arrows indicate the procedure of the operation. The hollow boxes indicate several main actions, and the hollow diamonds show main steps to complete the operation. The gray boxes indicate core hardware components of the apparatus. Communications from the controller to the hardware components are illustrated by dashed arrows and the responses of the hardware components to yield predefined functionalities are illustrated by thin arrows. The operation procedures of the nucleic acid analysis apparatus 100 are described as follows with reference to FIGS. 1 to 8.

In the first step, manual operations are performed. The top chamber 11 of the nucleic acid analysis apparatus 100 is opened. The sample is added to the cartridge 6 through the opening 624 on the detection chip 62, wherein the reagents for the sample purification and the nucleic acid extraction are preloaded in the reagent cells 631 of the reagent storing body 63. After the sample is added to the cartridge 6, the cartridge 6 is loaded into the bottom chamber 12. Once the cartridge 6 is placed into the cavity 121 of the bottom chamber 12, the positioning component 17 on the bottom chamber 12 helps the cartridge 6 self-aligned with the fluid delivery unit 2. In addition, by pushing the cartridge 6 downwardly, the cartridge 6 is locked by the clip 14 and forced to contact the fluid delivery unit 2 tightly. Then the top chamber 11 is closed to start sample processing.

In the second step, the sample purification and the nucleic acid extraction are performed. In this step, sample processing is carried out within the cartridge 6 and the reagents, such as biochemical buffers, are transported to each desired locations through the assistance of the fluid delivery unit 2. After the sample purification and the nucleic acid extraction are completed, the sample with extracted nucleic acid is transported to the detection wells 621 of the cartridge 6 for following nucleic acid amplification and/or detection.

In the third step, the chamber 1 is heated by the thermal unit 3. In this step, the heater 31 is turned on to provide heat. The rotational driven unit 4 drives the rotation of the fan blades 33 to blend the temperature inside the chamber 1 and generate air flow towards the heat spreader 32 to further accelerate the thermal mixing within the closed chamber 1. In addition, the temperature sensor is used to monitor the sample temperature.

In the fourth step, the nucleic acid amplification and the nucleic acid detection are performed. When the sample temperature reaches a predefined value, the fan blades 33 are ceased and the clip 14 is unlocked to release the cartridge 6, and meanwhile, the heater 31 is still in operation to maintain the temperature. Subsequently, the cartridge 6 is clamped by the cartridge clamp 41, and the isothermal based amplification is started. Once the cartridge 6 is clamped, it is able to rotate within the chamber 1, which is actuated by the rotational driven unit 4. The cartridge 6 is able to rotate with a certain angle so that the detection well 621 aligns with the optical unit 5 and stops for a short period (200 ms, for example) for detection. Thereby, each detection well 621 is able to pass through a series of light sources 51 with different colors and the emitted lights are able to be detected with the optical detectors 52, such as photodiode.

After the detection is completed, the detection results may be sent to cloud or digital devices, such as PC, tablet or smart phone, through USB or wireless. The chamber 1 is opened and the cartridge 6 is discarded.

In the above embodiments, the cartridge 6 is illustrated as one-in-one cartridge, which means one sample per detection. However, in another embodiment, the cartridge 6 may be X-in-one cartridge, which means X samples per detection. For example, the detection chip 62 could includes plural openings 624 for adding plural different samples into the same cartridge 6 to have flexible throughput (1~X), without increasing hardware cost.

In conclusion, the embodiment of the present invention provides an all-in-one nucleic acid analysis apparatus with isothermal based amplification, which integrates the fluid delivery unit, the thermal unit, the rotational driven unit and the optical unit on one single device, so that the processes of sample purification, nucleic acid extraction, nucleic acid amplification and nucleic acid detection can be performed on the all-in-one apparatus to realize nucleic acid analysis in real time. Therefore, the nucleic acid analysis apparatus provides an easy and fast nucleic acid analysis. Further, due to the arrangements of multiple detection wells and multiple optical units, both multiplexing nucleic acid analysis and multiple color multiplexing detection are achieved. In addition, since the thermal unit is significantly simplified, the nucleic acid analysis apparatus can be compact designed, so it is portable and suitable for POC diagnostics. Also, the cost for nucleic acid analysis is also reduced. Beside, the nucleic acid analysis apparatus has acceptable sensitivity and specificity, and flexible throughput as well.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A nucleic acid analysis apparatus, comprising:
a chamber comprising a cartridge mounted therein, wherein the cartridge comprises a detection chip and a reagent storing body, the detection chip comprises plural detection wells, and the reagent storing body comprises plural reagent cells used to store reagents for sample purification and/or nucleic acid extraction and plural channels connected with the reagent cells for fluid delivery;
a fluid delivery unit connected with the chamber and adapted to transport reagents within the cartridge for sample purification and/or nucleic acid extraction, wherein the fluid delivery unit comprises plural microchannels for connecting with the cartridge and a pump adapted to provide pneumatic force to transport the reagents stored within the cartridge;
a thermal unit disposed in the chamber and comprising a heater to provide a predefined temperature for nucleic acid amplification;
multiple optical units fixed on the chamber, each optical unit comprising a light source and an optical detector and offering a unique color of illumination to detect multiple targets; and
a rotational driven unit connected with the chamber and comprising a motor capable of rotating the cartridge with a predefined program,
wherein the chamber comprises at least one clip, and during sample purification and/or nucleic acid extraction, the cartridge is locked on the chamber by the at least one clip to contact the fluid delivery unit;
wherein the rotational driven unit comprises a cartridge clamp mounted on a shaft of the rotational driven unit to clamp the cartridge apart from the fluid delivery unit and rotate the cartridge to align the detection wells of the cartridge with the optical units during nucleic acid amplification and/or detection.

2. The nucleic acid analysis apparatus according to claim 1, wherein the chamber is able to be opened and comprises a top chamber and a bottom chamber.

3. The nucleic acid analysis apparatus according to claim 2, wherein the cartridge is mounted in a cavity of the bottom chamber.

4. The nucleic acid analysis apparatus according to claim 1, wherein the cartridge comprises a lock slot capable of being engaged with the clip.

5. The nucleic acid analysis apparatus according to claim 4, wherein the lock slot is disposed on a cylindrical surface of the reagent storing body.

6. The nucleic acid analysis apparatus according to claim 1, wherein the chamber further comprises a release actuator to unlock the cartridge.

7. The nucleic acid analysis apparatus according to claim 1, wherein the cartridge clamp comprises a magnet, and the cartridge comprises an embedded magnetic material, so that a magnetic force between the magnet and the magnetic material attracts the cartridge to move toward the cartridge clamp.

8. The nucleic acid analysis apparatus according to claim 1, wherein the motor comprises a step motor to rotate the cartridge at a predefined angle.

9. The nucleic acid analysis apparatus according to claim 1, wherein the shaft of the rotational driven unit and the cartridge clamp are in line with a central axis of the cartridge to clamp and rotate the cartridge during nucleic acid amplification and/or detection.

10. The nucleic acid analysis apparatus according to claim 9, wherein the cartridge clamp comprises a magnet, and the cartridge comprises an embedded magnetic material disposed on a central location of the detection chip in line with the cartridge clamp mounted on the shaft of the rotational driven unit, so that a magnetic force between the magnet and the magnetic material attracts the cartridge to move toward the cartridge clamp to clamp and rotate the cartridge during nucleic acid amplification and/or detection.

11. The nucleic acid analysis apparatus according to claim 1, wherein the thermal unit comprises a heat spreader, and plural fan blades.

12. The nucleic acid analysis apparatus according to claim 11, wherein the fan blades are mounted on and driven by the rotational driven unit, and a rotation of the fan blades generates air flow towards the heat spreader to accelerate the thermal mixing within the chamber.

13. The nucleic acid analysis apparatus according to claim 1, wherein detection chip is disposed on the top of the reagent storing body.

14. The nucleic acid analysis apparatus according to claim 13, wherein the detection chip is a planar fluidic chip and comprises the plural detection wells and at least one microchannel connected with the detection wells.

15. The nucleic acid analysis apparatus according to claim 14, wherein each of the detection wells has at least one planar surface.

16. The nucleic acid analysis apparatus according to claim 13, wherein the shape of the detection chip is substantially a regular polygon.

17. The nucleic acid analysis apparatus according to claim 13, wherein the chamber further comprises at least one positioning pin, and the detection chip comprises at least one alignment slot capable of being aligned with the at least one positioning pin on the chamber.

18. The nucleic acid analysis apparatus according to claim 13, wherein the detection chip further comprises at least one opening at a top surface of the detection chip for adding sample to the cartridge.

\* \* \* \* \*